United States Patent [19]

Sun

[11] Patent Number: 5,329,048

[45] Date of Patent: Jul. 12, 1994

[54] PROCESS OF PREPARING TETRAAMINO INTERMEDIATES

[75] Inventor: Jung-Hui Sun, Hockessin, Del.

[73] Assignee: The DuPont Merck Pharmaceutical Company, Wilmington, Del.

[21] Appl. No.: 25,633

[22] Filed: Feb. 16, 1993

Related U.S. Application Data

[60] Division of Ser. No. 805,044, Dec. 11, 1991, Pat. No. 5,206,249, which is a continuation-in-part of Ser. No. 676,061, Mar. 27, 1991, abandoned.

[51] Int. Cl.⁵ ........................................... C07C 209/50
[52] U.S. Cl. ................................... 564/488; 560/158; 564/138; 564/141
[58] Field of Search .................. 564/488, 138, 141; 560/158

[56] References Cited

U.S. PATENT DOCUMENTS

| | | | |
|---|---|---|---|
| 4,146,720 | 3/1979 | Roldan et al. | 546/99 |
| 4,665,071 | 5/1987 | Zee-Cheng et al. | 514/237 |
| 4,841,052 | 6/1989 | Harnisch et al. | 544/361 |
| 4,874,863 | 10/1989 | Brana et al. | 540/99 |
| 4,919,848 | 4/1990 | Harnisch | 252/600 |

FOREIGN PATENT DOCUMENTS

| | | |
|---|---|---|
| 0125439 | 11/1984 | European Pat. Off. |
| 0281902 | 9/1988 | European Pat. Off. |
| WO09850 | 7/1991 | PCT Int'l Appl. |
| WO9217453 | 10/1992 | PCT Int'l Appl. |

OTHER PUBLICATIONS

Complexes with Asymmetric Tetramine Ligands, Part 1., Muir et al., Synth. React. Inorg. Met.-Org. Chem., 11(4), 317–331 (1981).

Stereochemistry of Complexes of Multidentate Ligands. Part 1. Asperger, et al., Inorganic Chemistry, vol. 4, No. 10, Oct. 1965.

*Primary Examiner*—Richard L. Raymond
*Attorney, Agent, or Firm*—Blair Q. Ferguson

[57] ABSTRACT

This invention relates to bis-naphthalimides, including 2,2'-[1,2-ethanediylbis[imino(1-methyl-2,1-ethanediyl)]]-bis[5-nitro-1H-benz[de]isoquinoline-1,3(2H)-dione] and 2,2'-[1,2-ethanediylbis[imino(2-methyl-2,1-ethanediyl)]]-bis[5-nitro-1H-benz[de]isoquinoline-1,3(2H)-dione], processes for their preparation, pharmaceutical compositions containing them, and methods of using them to treat cancer in mammals.

1 Claim, No Drawings

PROCESS OF PREPARING TETRAAMINO INTERMEDIATES

This is a division of application Ser. No. 07/805,044, filed Dec. 11, 1991, now U.S. Pat. No. 5,206,249 which is a continuation-in-part of application Ser. No. 07/676,061, filed Mar. 27, 1991, now abandoned.

FIELD OF THE INVENTION

This invention relates to bis-naphthalimides, including 2,2'-[1,2-ethanediylbis[imino(1-methyl-2,1-ethanediyl)]]-bis[5-nitro-1H-benz[de]isoquinoline-1,3(2H)-dione] and 2,2'-[1,2-ethanediylbis[imino(2-methyl-2,1-ethanediyl)]]-bis[5-nitro-1H-benz-[de]isoquinoline-1,3(2H)-dione], processes for their preparation, pharmaceutical compositions containing them, and methods of using them to treat cancer, particularly solid tumor carcinomas, in mammals.

BACKGROUND OF THE INVENTION

Harnisch et al., U.S. Pat. No. 4,841,052 issued Jun. 20, 1989 describe naphthalic acid imides useful as charge-regulating substances in electrophotographic toners.

Brana et al., U.S. Pat. No. 4,874,863 issued Oct. 17, 1989 discloses anticancer compounds of the formula:

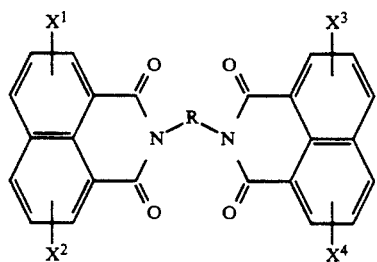

wherein $X^1$, $X^2$, $X^3$ and $X^4$ are identical or different and are each H, $NO_2$, $NH_2$, $C_1$-$C_6$-alkylamino, di-$C_1$-$C_6$-alkylamino, OH, $C_1$-$C_6$-alkoxy, halogen, trihalomethyl, $C_1$-$C_6$ alkyl, formyl, $C_1$-$C_6$-alkylcarbonyl, ureyl, $C_1$-$C_6$-alkylurely and R is a straight chain or branched $C_4$-$C_{10}$—alkylene which is interrupted at one or two points in the chain by a secondary or tertiary amino group, where 2 nitrogen atoms may additionally be bonded to one another by an alkylene group, or a salt with a physiologically tolerated acid.

DETAILED DESCRIPTION OF THE INVENTION

There is provided by this invention bis-naphthalimide compounds having the formula (i):

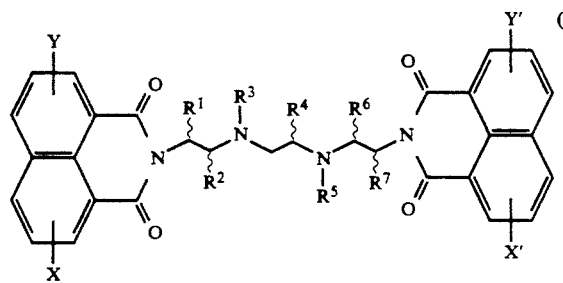

or enantiomeric or diastereomeric forms thereof, or mixtures of enantiomeric or diastereomeric forms thereof, or pharmaceutically acceptable salts thereof, wherein:

$R^1$, $R^2$, $R^3$, $R^4$, $R^5$, $R^6$, and $R^7$, independently, are H or $CH_3$;

X and X' are H or $NO_2$; and

Y and Y' are H or $NO_2$, provided that at least one of X, X', Y, and Y' is $NO_2$.

Preferred compounds of the present invention include those compounds of formula (i) wherein:

$R^1$ and $R^7$ are $CH_3$;

$R^2$, $R^3$, $R^4$, $R^5$, and $R^6$ are H;

X and X' are $NO_2$, wherein the substituent is at the 3-position of the naphthalimide (i.e., the 5-position of the 1H-benz[de]isoquinoline-1,3(2H)-dione); and Y and Y' are H.

Preferred compounds of the present invention also include those compounds of formula (i) wherein:

$R^2$ and $R^6$ are $CH_3$;

$R^1$, $R^3$, $R^4$, $R^5$, and $R^7$ are H;

X and X' are $NO_2$, wherein the substituent is at the 3-position of the naphthalimide (i.e., the 5-position of the 1H-benz[de]isoquinoline-1,3(2H)-dione); and Y and Y' are H.

Specifically preferred compounds of the present invention are the following:

(S,S)-2,2'-[1,2-ethanediylbis[imino(1-methyl-1,2-ethanediyl)]]-bis[5-nitro-1H-benz[de]isoquinoline-1,3(2H)-dione];

(Racemic+Meso)-2,2'-[1,2-ethanediylbis[imino(2-methyl-2,1-ethanediyl)]]-bis[5-nitro-1H-benz-[de]isoquinoline-1,3(2H)-dione];

(R,R)-2,2'-[1,2-ethanediylbis[imino(1-methyl-2,1-ethanediyl)]]-bis[5-nitro-1H-benz[de]isoquinoline-1,3(2H)-dione];

(Meso)-2,2'-[1,2-ethanediylbis[imino(1-methyl-2,1-ethanediyl)]]-bis[5-nitro-1H-benz[de]isoquinoline-1,3(2H)-dione];

(Racemic+Meso)-2,2'-[1,2-ethanediylbis[imino(2-methyl-2,1-ethanediyl)]]-bis[5-nitro-1H-benz-[de]isoquinoline-1,3(2H)-dione];

(R,R)-2,2'-[1,2-ethanediylbis[imino(2-methyl-2,1-ethanediyl)]]-bis[5-nitro-1H-benz[de]isoquinoline-1,3(2H)-dione]; or (Meso)-2,2'-[1,2-ethanediylbis[imino(2-methyl-2,1-ethanediyl)]]-bis[5-nitro-1H-benz[de]isoquinoline-1,3(2H)-dione];

and pharmaceutically acceptable salts thereof.

Also provided by this invention are processes for the preparation of the compounds of formula (i), pharmaceutical compositions containing the compounds of formula (i), and methods of using these compounds for the treatment of cancer, particularly solid tumor carcinomas, in a mammal.

Synthesis

The present invention describes a series of bis-naphthalimides useful for treating cancer containing linkers derived from reduced peptides. Compounds of this invention are more soluble in aqueous media than prior art compounds not containing these reduced peptide linkers.

Compounds of this invention can be synthesized by reacting two equivalents of an anhydride of formula (ii) with one equivalent of a polyamine of formula (iii) in an inert solvent such as ethanol or dimethylformamide or tetrahydrofuran, for example, at a temperature ranging from ambient to the solvent's boiling temperature (Scheme A). The resulting suspension can then be filtered to give the free base of (i) or it can be acidified with the appropriate mineral or organic acid to produce a pharmaceutically acceptable salt, which can be obtained by filtration. Salts of the free base can also be prepared by acidifying a suspension of the free base in ethyl alcohol or dichloromethane with the appropriate mineral or organic acid and collecting the formed solid by filtration. In some cases, the free base of (i) requires purification by column chromatography before its salt can be prepared as described above.

Scheme A

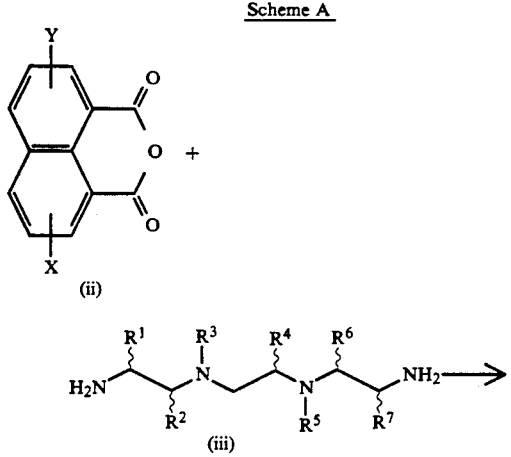

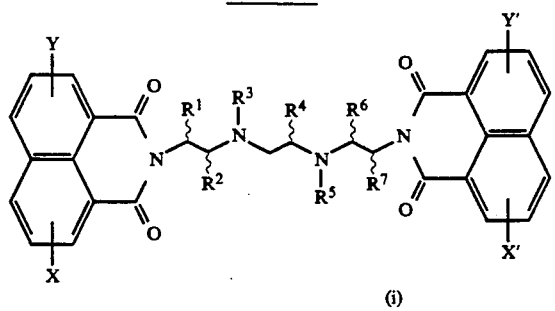

The parent anhydride (ii) is commercially available or can be prepared according to the procedures described by Hodgson et al., J. Chem. Soc., p. 90 (1945). Reduced peptides of formula (iii) can be prepared according to the methods described below (Schemes I–IV).

The synthesis of compounds of formula Va, (see Scheme I below) can be accomplished by the reaction of t-BOC-(S)-alanine (compound a) with 1,1'-carbonyl-diimidazole, followed by reaction with ethylenediamine under standard conditions. Acid hydrolysis of the t-BOC (N-tert-butoxycarbonyl) protecting group in Ia was performed under standard conditions to afford IIa. The same procedure is utilized to produce compounds IIb or IIc by starting the sequence with the corresponding (R)-alanine (compound b) or racemic alanine (compound c).

Reduction of IIa (dihydrochloride salt) with diborane in tetrahydrofuran at refluxing temperature afforded IIIa. IIIa was then neutralized with sodium ethoxide and the pure free base IVa was obtained by Kugelrohr distillation. IVa was reacted with the appropriate naphthalic anhydride in ethanol or tetrahydrofuran at reflux temperature to obtain Va. Compounds Vb and Vc are prepared similarly by using the corresponding IVb, or IVc, respectively.

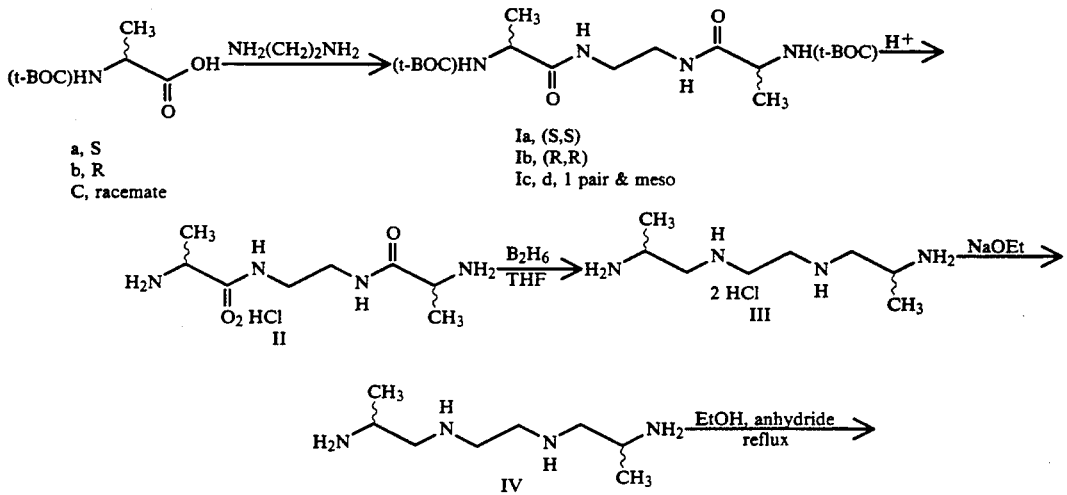

-continued
Scheme I

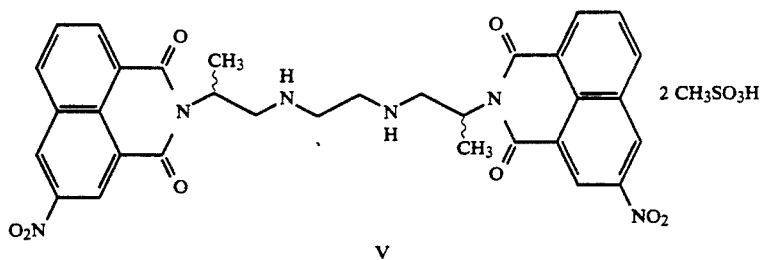

Bis-naphthalimides of the formula (XIX) where $R^1=R^3=R^4=R^5=R^7=H$, $R^2=R^6=CH_3$ and X and Y are $NO_2$ or H can be made by Scheme III. Reaction of (S)-alanine methyl ester with oxalyl chloride in benzene at reflux temperature gave amide XVa. Amide XVa was converted to amide XVIa with ammonia in methanol under standard conditions. Amide XVIa was reduced with diborane in tetrahydrofuran to yield amine XVIIa as the tetrahydrochloride salt which was subsequently neutralized with sodium ethoxide to yield the free amine XVIIIa. Amine XVIIIa was condensed with the appropriate naphthalic anhydride to produce compound XIXa. Compounds XIXb and XIXc could be prepared similarly by using the corresponding compounds XVIIIb and XVIIIc, respectively. In addition, compounds XXa, XXVIIIb and XXIXb could be prepared by condensation of amine XVIIIb with appropriate naphthalic anhydrides.

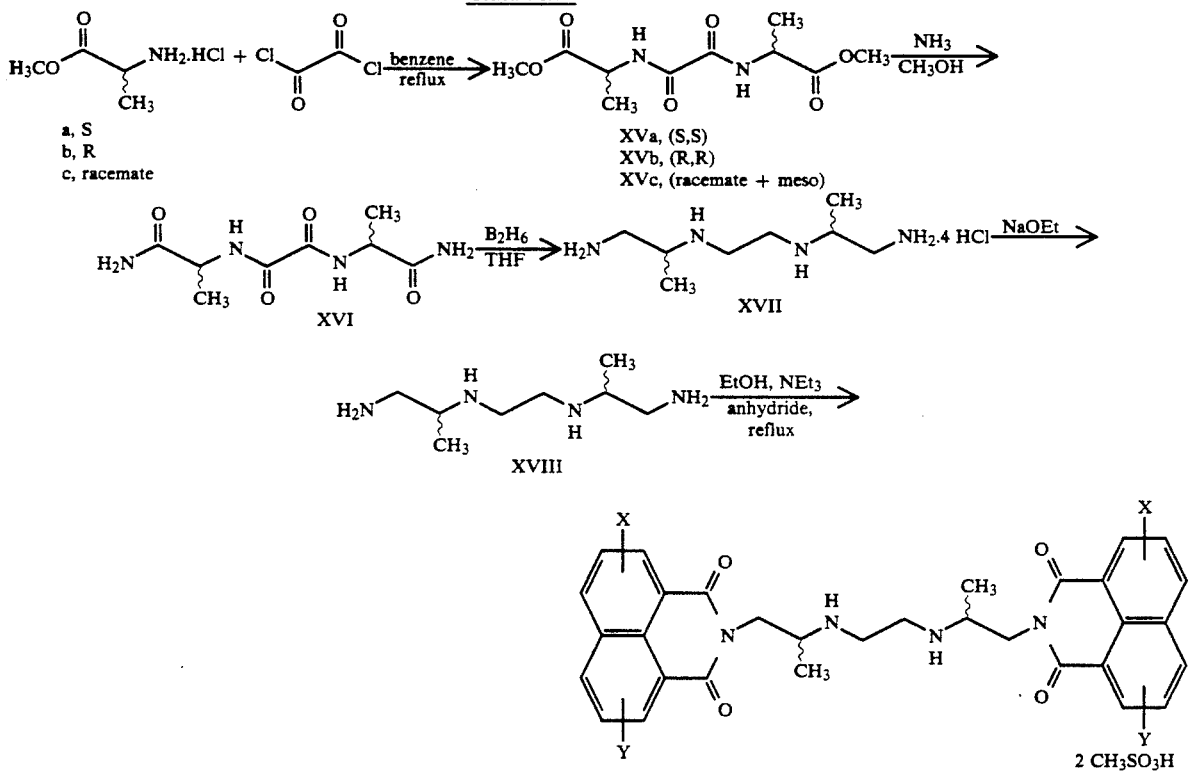

| | | |
|---|---|---|
| XIXa, | X = 3-NO₂, Y = H | (S,S) |
| XIXb, | X = 3-NO₂, Y = H | (R,R) |
| XIXc, | X = 3-NO₂, Y = H | (racemate + meso) |
| XXa, | X = Y = H | (S,S) |
| XXVIIIb, | X = 4-NO₂, Y = H | (R,R) |
| XXIXb, | X = 3-NO₂, Y = 6-NO₂ | (R,R) |
| XXXIV, | X = 3-NO₂, Y = H | (racemate) |

In Scheme III the position of X and Y is indicated using the numbering for the position in the corresponding naphthalic anhydride, and not the numbering for the 1H-benz[de]isoquinoline-1,3(2H)-dione.

For compounds of the formula (XXVII), the synthesis is shown in Scheme IV. Reaction of t-BOC-(S)-alanine with isobutylchloroformate in the presence of N-methylmorpholine, followed by reaction with aminoacetonitrile (generated by neutralization of its HCl salt with N-methylmorpholine), gave XXI. This was hydrogenated with palladium hydroxide in acetic acid to yield XXII. Reaction of t-BOC-(R)-alanine with 1,1'-carbonyldiimidazole, followed by addition of XXII under standard conditions, afforded XXIII. Acid hydrolysis of the t-BOC protecting group of XXIII was carried out under standard conditions to furnish XXIV. Subsequent reduction with diborane in refluxing tetrahydrofuran yielded XXV, which was neutralized with sodium ethoxide to give XXVI. Amine XXVI was condensed with the appropriate naphthalic anhydride to produce XXVII.

of N-methylmorpholine, followed by addition of (S)-alanine methylester hydrochloride to give XXXV. The ester XXXV was converted to its amide XXXVI by bubbling ammonia in methanol. The t—BOC protecting group was removed by acid hydrolysis to furnish XXXVII. Subsequent diborane reduction of tripeptide amide XXXVII in refluxing tetrahydrofuran yielded the polyamine tetrahydrochloride XXXVIII, which

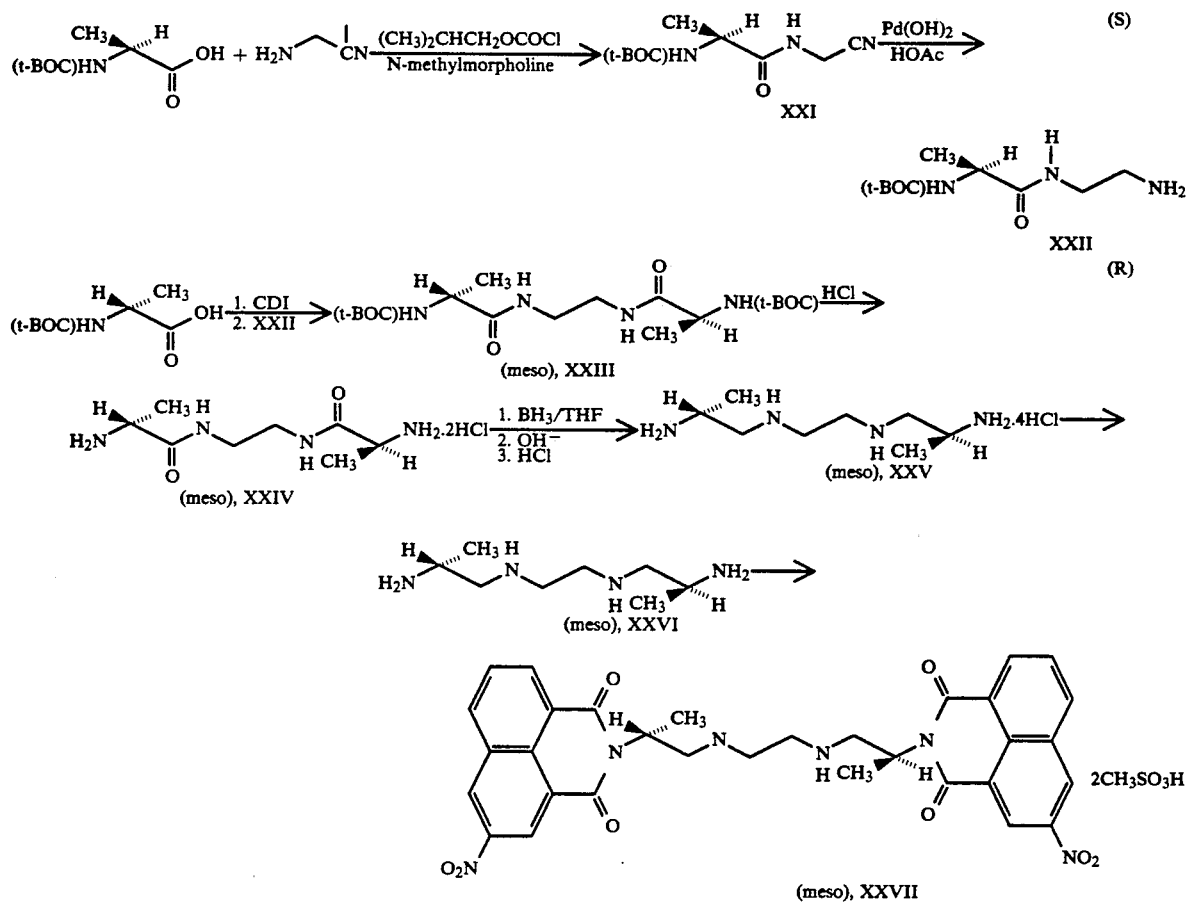

For compounds of the formula (XXXX), the synthesis is shown in Scheme V (below). (t-BOC)-Alaninyl alanine was reacted with isobutyl chloroformate in methylene chloride at −10° to −15° C. in the presence was neutralized with sodium ethoxide to yield XXXIX. The amine XXXIX was condensed with the appropriate naphthalic anhydride to produce XXXX.

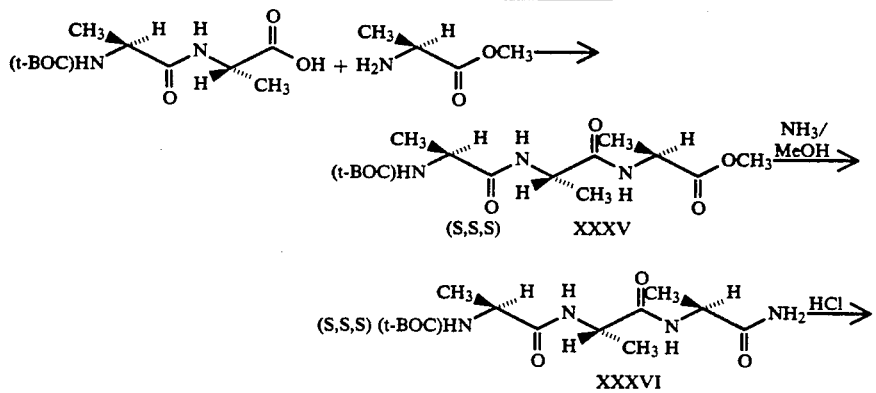

Scheme V

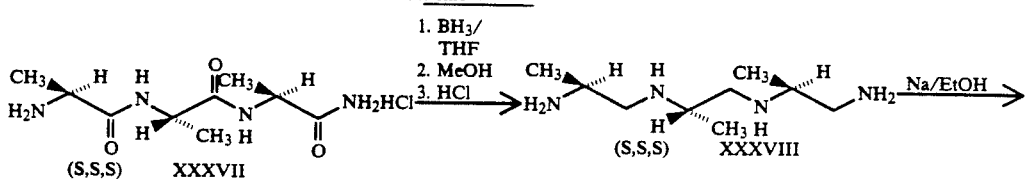

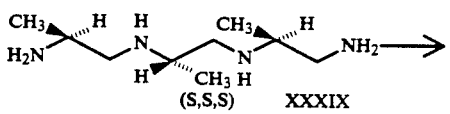

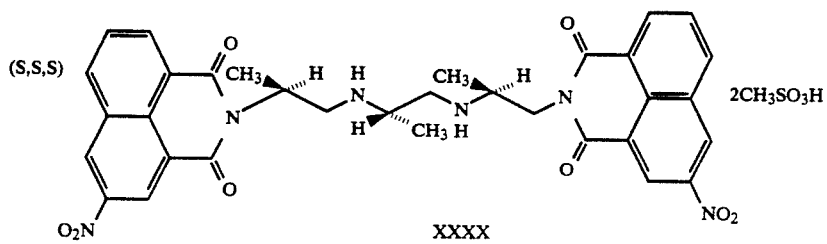

Asymmetric bis-naphthalimides of the formula (XXXXVI) can be synthesized as shown in Scheme VI (below). Reaction of XXII with 1,1'-carbonyldiimidazole, followed by addition of (R)-benzyloxycarbonyl alanine, furnished XXXXI. Subsequent reaction with phosphorus pentasulfide in tetrahydrofuran gave the corresponding thioamide XXXXII. Treatment of XXXXII with Raney Nickel yielded amine XXXXIII.

Amine XXXXIII was condensed with 3-nitro-1,8-naphthalic anhydride to yield naphthalimide XXXXIV. The (t-BOC) protecting group was hydrolyzed under standard conditions to give XXXXV, which in turn can be condensed with another naphthalic anhydride to produce non-symmetric bis-naphthalimides of the formula XXXXVI.

Scheme VI

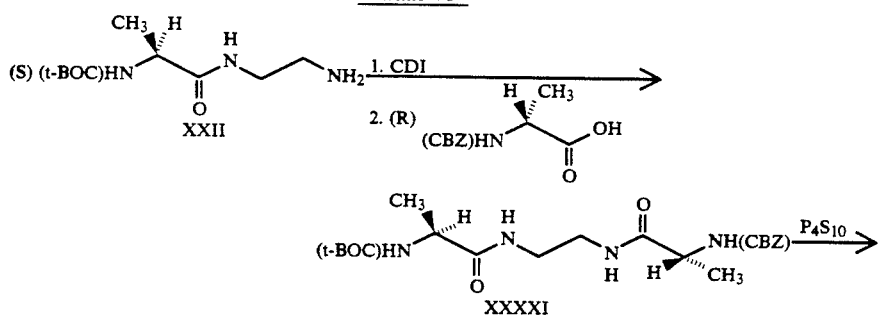

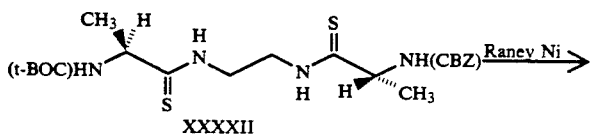

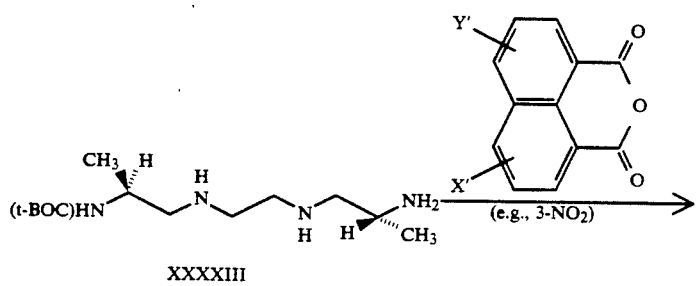

Scheme VI -continued

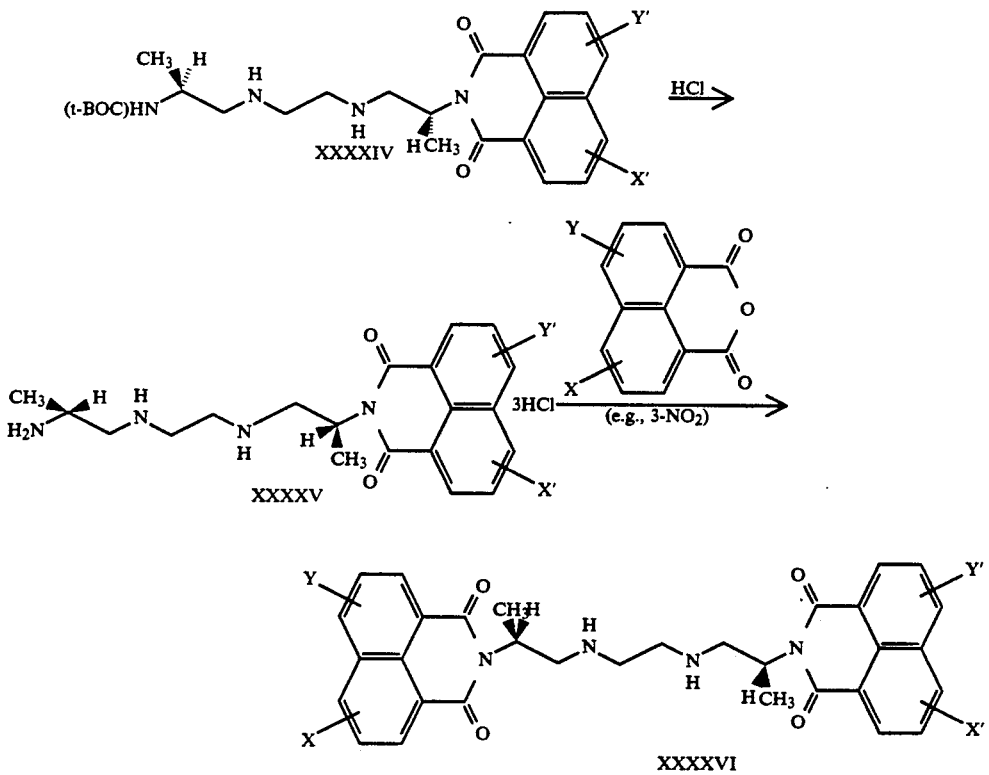

The invention can be further understood by referring to the following Examples and Tables below.

EXAMPLE 1

(S,S)-2,2'-[1,2-ethanediylbis[imino(1-methyl-2,1-ethanediyl)]]-bis[5-nitro-1H-benz[de]isoquinoline-1,3(2H)-dione] methanesulfonate (1:2) (Va)

Part A: (IIIa) (S,S)-$N^1,N^{1'}$-1,2-ethanediylbis[1,2-propanediamine] tetrahydrochloride.

To a THF (80 ml) suspension of IIa (2.75 g, 10 mmol), there was added 200 ml of 1M $BH_3$.THF complex slowly. The mixture was stirred at room temperature for 1½ hours and then heated overnight to become a clear solution. After cooling to room temperature, the solution was carefully quenched with 100 ml of methanol, and then refluxed overnight. The solvent was evaporated, and to the remaining liquid was added 20 ml of methanol and 5 ml of conc. HCl. The resulting white solid was collected on a filter under nitrogen to give 1.92 g (60%) of IIIa; mp 210°–215° C. $^1$H-NMR ($D_2O$) δ3.60 (m, 2H, 2 CH), 3.40 (s, 4H, 2 $CH_2$), 3.27 (m, 4H, 2 $CH_2$) and 1.30 (d, 6H, J=6.9 Hz, 2 $CH_3$). MS (DCI) m/e 175 (M+1, free base). [α]$_D$−2.31° (c=0.606, $H_2O$).

Part B: (IVa) (S,S)-$N^1$, $N^{1'}$-1,2-ethanediylbis[1,2-propanediamine].

Sodium (1.03 g, 45 mmol) was added to 50 ml of anhydrous ethanol; and the mixture stirred for 1.5 hours until all the sodium was dissolved. To this, there was added 3.2 g (10 mmol) of IIIa. After stirring for 2 hours, the sodium chloride precipitate was removed by filtration; and the solvent in the filtrate evaporated. Kugelrohr distillation (120°–140° C. at 1.4 mm) gave 1.29 g (74%) of IVa as a clear liquid. $^1$H-NMR ($CDCl_3$) δ2.96 (m, 2H, 2 CH), 2.71 (m, 4H, 2 $CH_2$), 2.60 (m, 2H, $CH_2$), 2.40 (m, 2H, $CH_2$), 1.46 (broad, 6H, 2 $NH_2$ and 2 NH) and 1.06 (d, 6H, J=6.2 Hz, 2 $CH_3$). MS (DCI) m/e 175 (M+1).

Part C: (Va) (S,S)-2,2'-[1,2-ethanediylbis[imino(1-methyl-2,1-ethanediyl)]]-bis[5-nitro-1H-benz[de]isoquinoline-1,3(2H)-dione] methanesulfonate (1:2).

A mixture of 3-nitro-1,8-naphthalic anhydride (2.43 g, 10 mmol) and IVa (0.87 g, 5 mmol) was stirred at room temperature for 4 hours, refluxed for 2 hours and then cooled to room temperature overnight. The solvent in the mixture was evaporated and the residue purified by column chromatography to give 0.87 g (27.9%) of a brown solid. The free base (0.84 g, 1.3 mmol) in 70 ml of methylene chloride was added 0.26 g of methanesulfonic acid. After stirring at room temperature overnight, the solvent in the mixture was evaporated, and 45 ml of methanol was added to the residue. After refluxing for 2 hours. the yellow solid was collected on a filter, dried in vacuo at 78° C. for 2 hours to give 0.86 g (81%) of Va mp 212°–213° C. (dec). $^1$H-NMR (DMSO-$d_6$) δ9.53 (d, 2H, J=2.2 Hz, aromatic protons), 8.96 (d, 2H, J=2.2 Hz, aromatic protons), 8.83 (d, 2H, J=7.7 Hz, aromatic protons), 8.69 (d, 2H, J=7.3 Hz, aromatic protons), 8.7–8.8 (broad, 4H, 2 $NH_2^+$), 8.09 (t, 2H, J=7.9 Hz, aromatic protons), 5.46 (m, 2H, 2 CH), 3.86 (m, 2H), 3.2–3.5 (m, 6H), 2.20 (s, 6H, 2 $CH_3$) and 1.57 (d, 6H, J=6.9 Hz, 2 $CH_3$). MS (DCI) m/e 625 (M+1). Anal. Calcd for $C_{32}H_{28}N_6O_8$.2 $CH_3SO_3H$ (MW 816.81): C, 50.00; H, 4.44; N, 10.29; S, 7.85. Found: C, 49.88; H, 4.39; N, 10.14; S, 7.86.

Similarly, Examples 2 and 3 may be prepared and characterized.

EXAMPLE 2

(racemate+meso)-2,2'-[1,2-ethanediylbis[imino(1-methyl-2,1-ethanediyl)]]-bis[5-nitro-1H-benz[de]isoquinoline-1,3(2H)-dione] methanesulfonate (1:2) (Vc)

Light yellow solid (18% yield); mp 220°-221° C. (dec). $^1$H-NMR of Vc is almost identical with that of Va except that Vc shows d of d at δ1.59 ppm due to the presence of dl pair and meso. MS(DCI) m/e 625 (M+1). Anal. Calcd for $C_{32}H_{28}N_6O_8 \cdot 2\ CH_3SO_3H \cdot H_2O$ (MW 834.83): C, 48.92; H, 4.59; N, 10.07; S, 7.68. Found: C, 49.10, 49.01; H, 4.45, 4.40; N, 10.02, 9.96; S, 7.39, 7.45.

EXAMPLE 3

(R,R)-2,2'-[1,2-ethanediylbis[imino(1-methyl-2,1-ethanediyl)]]-bis[5-nitro-1H-benz[de]isoquinoline-1,3(2H)-dione] methanesulfonate (1:2) (Vb)

Light yellow solid (25% yield); mp 210°-211° C. (dec). The $^1$H-NMR of Vb is identical with that of Va. MS (DCI) m/e 625 (M+1). Anal. Calcd for $C_{32}H_{28}N_6O_8 \cdot 2\ CH_3SO_3H$ (MW 816.81): C, 50.00; H, 4.44; N, 10.29; S, 7.85. Found: C, 49.98; H, 4.41; N, 10.14; S, 7.81.

EXAMPLE 26

(Meso)-2,2'-[1,2-ethanediylbis[imino(1-methyl-2,1-ethanediyl)]]-bis[5-nitro-1H-benz[de]isoquinoline-1,3(2H)-dione] methanesulfonate (1:2) (XXVII)

Part A: (XXI) 1,1-Dimethylethyl-(S)-[2-[(cyanomethyl)amino]-1-methyl-2-oxoethyl]carbamate.

A mixture of aminoacetonitrile hydrochloride (9.25 g, 100 mmol) and N-methylmorpholine (10.1 g, 100 mmol) in 100 ml of THF was stirred for 15 minutes. N-t-BOC-(S)-alanine (18.9 g, 100 ml) and N-methylmorpholine (10.1 g, 100 mmol) in 100 ml of THF was stirred with an ice-salt bath. Isobutyl chloroformate (12.97 ml, 100 mmol) was added at such a rate that the temperature of the mixture won't exceed 10° C. and the mixture of the nitrile-N-methylmorpholine suspension was added after 2 minutes. The mixture was stirred at room temperature overnight. The N-methylmorpholine hydrochloride was removed by filtration and the solvent in the filtrate was evaporated. The remaining liquid was diluted with methylene chloride (500 ml), washed with aq. $K_2CO_3$ (2×100 ml), $H_2O$ (1×100 ml). The layers were separated; and the organic layer dried over anhydrous $MgSO_4$, filtered and evaporated to give 15.85 g (69.7%) of the crude product. This was purified by column chromatography to give pure XXI (14.88 g, 65.5%), mp 99°-100° C. $^1$H-NMR (CDCl$_3$) δ7.32 (broad, 1H, NH), 5.12 (d, 1H, J=5.8 Hz, NH), 4.15 (m, 3H, CH and CH$_2$), 1.46 (s, 9H, 3 CH$_3$) and 1.39 (d, 3H, J=7.0 Hz, CH$_3$). MS (CI) m/e 228 (M+1).

Part B: (XXII) 1,1-dimethylethyl-(S)-[2-[(2-aminoethyl)amino]-1-methyl-2-oxoethyl]carbamate.

A mixture of XXI (2.0 g, 8.8 mmol) and palladium hydroxide (0.5 g) in 15 ml of acetic acid was hydrogenated (50 psi) in a Parr shaker for 1½ hours. The catalyst in the mixture was removed by filtration. The acetic acid in the filtrate was removed by vacuum distillation to give a light yellow viscous liquid, which was added 15 ml of methanol and 1 g of sodium bicarbonate. The mixture was stirred at room temperature for several hours. The sodium acetate was removed by filtration; and the solvent in the filtrate evaporated to give the crude product. This was purified by column chromatography to give pure XXII (0.92 g, 45.2%) as a viscous liquid. $^1$H-NMR (CDCl$_3$) δ7.08 (broad, 1H, NH), 5.28 (broad, 1H, NH), 3.28-3.26 (m, 2H, CH$_2$), 2.84 (t, 2H, J=5.9 Hz, CH$_2$), 1.41 (S, 9H, 3 CH$_3$) and 1.34 (d, 3H, J=6.9 Hz, CH$_3$). MS (CI) m/e 232 (M+1).

Part C: (XXIII) 1,1-Dimethylethyl (meso)-[1,2-ethanediylbis[imino(1-methyl-2-oxo-2,1-ethanediyl)]]-bis(carbamate).

A mixture of N-t-BOC-(R)-alanine (0.74 g, 3.9 mmol) and 1,1'-carbonyldiimidazole (0.64 g, 3.9 mmol) in 20 ml of methylene chloride was stirred with an ice bath cooling for 1½ hours. To this, there was added XXII (0.91 g, 3.9 mmol) in 10 ml of methylene chloride with an ice bath cooling. The mixture was stirred at ambient temperature overnight. The product was collected on a filter to give XXIII (1.22 g, 77.9%) as a white solid. $^1$H-NMR (DMSO-d$_6$) δ7.83 (broad, 2H, 2 NH), 6.85 (m, 2H, 2 NH), 3.90 (m, 2H, 2 CH), 3.13 (m, 4H, 2 CH$_2$), 1.40 (s, 10H, 6 CH$_3$) and 1.18 (d, 6H, 2 CH$_3$). MS (CI) m/e 403 (M+1).

Part D: (XXIV) (Meso)-N,N'-1,2-ethanediylbis[2-aminopropanamide] dihydrochloride.

A mixture of XXIII (1.18 g, 2.9 mmol) and 2.7 ml of 4.4 N HCl in 40 ml of dioxane was heated to reflux for 5 hours and then cooled to room temperature overnight. The solvent in the mixture was evaporated to give XXIV (0.75 g, 94%) as a white solid. $^1$H-NMR (DMSO-d$_6$) δ8.81 (broad, 2H, 2 NH), 8.33 (broad, 4H, 2 NH$_2$), 3.83 (q, 2H, J=6.9 Hz, 2 CH), 3.21 (broad s, 4H, 2 CH$_2$) and 1.37 (d, 6H, J=6.9 Hz, 2 CH$_3$).

Part E: (XXV) (Meso)-N$^1$,N$^{1'}$-1,2-ethanediylbis[1,2-propanediamine]tetrahydrochloride To 30 ml or 1M borane THF complex, there was added 0.75 g (2.7 mmol) of XXIV. The mixture was refluxed overnight. After cooling to room temperature, methanol (15 ml) was added slowly to the reaction mixture. The mixture was then refluxed for 3 days. The solvents in the mixture were evaporated. To the residue was added 20 ml of methanol and 1.5 ml of conc. HCl. The mixture was stirred at room temperature for 4 hours, and then the solvent and excess HCl evaporated to give XXV (0.81 g, 93.7%) as a white solid. $^1$H-NMR (D$_2$O) δ3.66 (m, 2H, 3.37 (s, 4H), 3.24 (m, 4H) and 1.29 (d, 6H, J=7.0 Hz, 2 CH$_3$). MS (CDI) m/e 175 (M+1).

Part F: (XXVI) (Meso)-N$^1$,N$^{1'}$-1,2-ethanediylbis[1,2-propanediamine]

To a freshly prepared solution of sodium ethoxide in ethanol (0.26 g of sodium in 40 ml of ethanol) was added 0.81 g of XXV. The mixture was stirred at room temperature for 1 hour. The sodium chloride was removed by filtration; and the solvent in the filtrate evaporated. The product was isolated from the residue by Kugelrohr distillation (88°-96° C. at 0.4 mm) to give XXVI (0.32 g, 73.4%) as a clear liquid. $^1$H-NMR (CDCl$_3$) δ2.88 (m, 2H, 2 CH), 2.63 (m, 4H, 2 CH$_2$), 2.48 (m, 2H, CH$_2$), 2.29 (m, 2H, CH$_2$), 1.54 (broad s, 6H, 2 NH$_2$ and 2 NH) and 0.96 (d, 6H, J=6.2 Hz, 2 CH$_3$). MS (CI) m/e 175 (M+1).

Part G: (XXVII) (Meso)-2,2'-[1,2-ethanediylbis[imino(1-methyl-2,1-ethanediyl)]]-bis[5-nitro-1H-benz[de]isoquinoline-1,3(2H)-dione]methanesulfonate (1:2).

A mixture of 3-nitro-1,8-napthalic anhydride (0.78 g, 3.2 mmol) and XXVI (0.28 g, 1.6 mmol) in 25 ml of ethanol was stirred at room temperature overnight and then heated to reflux for 2⅔ hours. The solvent in the mixture was evaporated to give the crude products.

This was purified by column chromatography to give pure product (0.39 g, 39%) as its free base. This was converted to its methanesulfonate salt, XXVII (0.33 g, 25.3%); mp 243°–244.5° C. (dec). $^1$H-NMR (DMSO-$d_6$) δ9.53 (s, 2H, aromatic protons), 8.96 (s, 2H, aromatic protons), 8.82 (d, 2H, J=8.0 Hz, aromatic protons), 8.77, 8.74 (broad, 4H, 2 NH$_2$+), 8.70 (d, 2H, J=6.9 Hz, aromatic protons), 8.09 (t, 2H, J=7.7 Hz, aromatic protons), 5.47 (m, 2H, 2 CH), 3.87 (m, 2H), 3.43 (m, 2H), 3.27 (broad, 4H), 2.20 (s, 6H, 2 CH$_3$SO$_3$H) and 1.58 (d, 6H, J=6.6 Hz, 2 CH$_3$). IR (KBr) 3445 (NH), 1770, 1668 (C=O) cm$^{-1}$. MS (DCI) m/e 625 (M+1). Anal. Calcd for C$_{32}$H$_{28}$N$_6$O$_8$.2CH$_3$SO$_3$H.½H$_2$O (MW 826.53): C, 49.41; H, 4.60; N, 10.17; S, 7.76. Found: C, 49.45, 49.41; H, 4.33, 4.29; N, 10.11, 10.21; S, 7.50, 7.58.

EXAMPLE 27

(S,S)-2,2'-[1,2-ethanediylbis[imino(2-methyl-2,1-ethanediyl)]]-bis[5-nitro-1H-benz[de]isoquinoline-1,3(2H)-dione] methanesulfonate (1:2) (XIXa)

Part A: (XVa) Dimethyl N,N'-1,2-dioxo-1,2-ethanediyl)bis[S-alanine].

A mixture of (S)-alanine methyl ester hydrochloride (14 g, 100 mmol) and oxalyl chloride (4.9 ml, 55 mmol) in 150 ml of benzene was refluxed overnight. After cooling to room temperature, the white solid was collected on a filter to give 12.36 g (95%) of XVa; mp 167°–170° C. $^1$H-NMR (DMSO-$d_6$) δ9.15 (d, 2H, 2 NH) 4.40 (quintet, 2H, 2 CH), 3.67 (s, 6H, 2 OCH$_3$) and 1.40 (d, 6H, 2 CH$_3$). MS (DCI) m/e 261 (M+1). [α]$_D$ −65.32° (c=1.012, AcOH).

Part B: (XVIa) (S,S)-N,N'-bis(2-amino-1-methyl-2-oxo-ethyl)ethanediamine.

Compound XVa (5.21 g, 20 mmol) was added to a methanol solution saturated with ammonia with an ice bath cooling. The mixture was further bubbled with ammonia for 1 hour; and then stirred at room temperature overnight. The white solid was collected on a filter to give 3.65 g (79%) of XVIa. $^1$H-NMR (DMSO-$d_6$) δ8.50 (d, 2H, J=7.7 Hz, 2 NH), 7.50 (s, 2H, NH$_2$), 7.21 (s, 2H, NH$_2$), 4.25 (quintet, 2H, J=7.3 Hz, 2 CH) and 1.31 (d, 6H, J=7.3 Hz, 2 CH$_3$). MS (DCI) m/e 231 (M+1). [α]$_D$ +69.14°(c=0.418, DMF).

Part C: (XVIIa) (S,S)-N$^2$,N$^{2'}$-1,2-ethanediylbis[1,2-propanediamine] tetrahydrochloride.

To a mixture of XVIa (3.5 g, 15.2 mmol) in 100 ml of THF, there was added 150 ml of 1M BH$_3$.THF complex. After refluxing overnight, the reaction mixture was cooled to room temperature and 80 ml of methanol was added slowly. The mixture was refluxed overnight, and a small amount of precipitate present were removed by filtration. The solvents in the filtrate were evaporated; and to the remaining liquid was added 30 ml of methanol and 7.5 ml of conc. HCl with an ice bath cooling. After stirring for 1.5 hours, the mixture was triturated with ethyl ether; and the product was collected on a filter to give 3.92 g (81%) of XVIIa; $^1$H-NMR (D$_2$O) δ3.54 (m, 2H, 2 CH), 3.31 (m, 6H), 3.06 (m, 2H) and 1.28 (d, 6H, J=6.6 Hz, 2 CH$_3$). MS(DCI) m/e 175 (M+1, free base). [α]$_D$ +8.39° (c=0.632, H$_2$O).

Part D: (XVIIIa) (S,S)-N$^2$,N$^{2'}$-1,2-ethanediylbis[1,2-propanediamine].

Compound XVIIa (3.2 g, 10 mmol) was added to a freshly prepared sodium ethoxide solution in ethanol (1.03 g of sodium in 50 ml of ethanol). After stirring at room temperature overnight, sodium chloride in the mixture was removed by filtration, and the solvent in the filtrate evaporated. The remaining mixture was purified by Kugelrohr distillation (110°–124° C. at 0.7 mm) to give 1.43 g (82%) of XVIIIa as a clear liquid. $^1$H-NMR (CDCl$_3$) δ2.8–2.4 (m, 10H, 4 CH$_2$ and 2 CH), 1.57 (broad, 6H, 2 NH$_2$ and 2 NH) and 0.91 (d, 6H, J=5.9 Hz, 2 CH$_3$). [α]$_D$ +120° (c=0.310, benzene).

Part E: (XIXa) (S,S)-2,2'-[1,2-ethanediylbis[imino(2-methyl-2,1-ethanediyl)]]-bis[5-nitro-1H-benz[de]isoquinoline-1,3(2H)-dione] methanesulfonate (1:2).

A mixture of 3-nitro-1,8-naphthalic anhydride (1.46 g, 6.0 mmol) and XVIIIa (0.52 g, 3 mmol) in 30 ml of ethanol was stirred at room temperature overnight. To this, there was added 0.63 g of methanesulfonic acid. After stirring overnight, the product was isolated by filtration and purified by heating in 50 ml of methanol overnight to give 1.37 g (55%) of XIXa; mp 254°–255° C. (dec). $^1$H-NMR (DMSO-$d_6$) δ9.55 (d, 2H, J=1.9 Hz, aromatic protons), 9.0 (d, 2H, J=1.9 Hz, aromatic protons), 8.85 (d, 2H, J=8.1 Hz, aromatic protons), 8.73 (d, 2H, J=7.0 Hz, aromatic protons), 8.11 (t, 2H, J=7.9 Hz, aromatic protons), 4.39–4.27 (m, 4H, 2 CH$_2$), 3.75 (m, 2H, 2 CH), 2.26 (s, 6H, 2 CH$_3$) and 1.35 (d, 6H, J=5.9 Hz, 2 CH$_3$). MS (DCI) m/e 625 (M+1). Anal. Calcd for C$_{32}$H$_{28}$N$_6$O$_8$.2CH$_3$SO$_3$H.H$_2$O (MW 834.83): C, 48.92; H, 4.59; N, 10.07; Found: C, 48.97, 48.84;H, 4.43, 4.46; N, 10.16, 10.13; S, 7.83, 7.84.

EXAMPLE 28

(S,S)-2,2'-[1,2-ethanediylbis[imino(2-methyl-2,1-ethanediyl)]]-bis[1H-benz[de]isoquinoline-1,3(2H)-dione] methanesulfonate (1:2) (XXa)

By replacing 3-nitro-1,8-naphthalic anhydride with 1,8-naphthalic anhydride, compound XXa can be prepared.

White solid (78% yield); mp 289°–290° C. (dec). $^1$H-NMR (DMSO-$d_6$) δ8.96 (broad, 2H, NH$_2$+), 8.80 (broad, 2H, NH$_2$+), 8.57–8.53 (m, 8H, aromatic protons), 7.94 (t, 4H, J=7.7 Hz, aromatic protons), 4.45–4.23 (m, 4H, 2 CH$_2$), 3.81 (m, 2H, 2 CH), 2.28 (s, 6H, 2 CH$_3$) and 1.36 (d, 6H, J=6.6 Hz, 2 CH$_3$). MS (DCI) m/e 535 (M+1, free base). Anal. Calcd for C$_{32}$H$_{30}$N$_4$O$_4$.2CH$_3$SO$_3$H.H$_2$O (MW 744.83): C, 54.83; H, 5.41; N, 7.42; S, 8.61. Found: C, 55.18, 55.29; H, 5.17, 5.24; N, 7.42, 7.47; S, 8.66, 8.64.

EXAMPLE 29

(R,R)-2,2'-[1,2-ethanediylbis[imino(2-methyl)-2,1-ethanediyl)]-bis[5-nitro-1H-benz[de]isoquinoline-1,3(2H)-dione]-methanesulfonate (1:2) (XIXb)

Light brown solid (34.5% yield); mp 248°–251° C. (dec). $^1$H-NMR (DMSO-$d_6$) δ9.54 (d, 2H, J=2.2 Hz, aromatic protons), 8.99 (d, 2H, J=1.9 Hz, aromatic protons), 8.83 (d, 2H, J=8.0 Hz, aromatic protons), 8.72 (d, 2H, J=6.9 Hz, aromatic protons), 8.10 (t, 2H, J=7.9 Hz, aromatic protons), 4.33–4.18 (m, 4H, 2 CH$_2$), 3.46 (m, 6H), 2.28 (s, 6H, 2 CH$_3$) and 1.28 (m, 6H, 2 CH$_3$). MS(Cl) m/e 625 (M+1). Anal. Calcd for C$_{32}$H$_{28}$N$_6$O$_8$.2CH$_3$SO$_3$H (MW 816.81) C, 50.00; H, 4.44; N, 10.09; S. 7.85. Found: C, 50.16; H, 4.34; N, 10.19; S, 7.62.

EXAMPLE 30

(Racemic+Meso)-2,2'-[1,2-ethanediylbis[imino[2-methyl-2,1-ethanediyl]-bis[5-nitro-1H-benz[de]isoquinoline-1,3(2H)-dione]-methanesulfonate (1:2) (XIXc)

Yellow solid (18.9% yield); mp 278°–281° C. (dec). $^1$H-NMR (DMSO-$d_6$) δ9.58 (d, 2H, aromatic protons), 9.0 (d, 2H, aromatic protons), 8.85 (d, 2H, aromatic protons), 8.75 (d, 2H, aromatic protons), 8.13 (t, 2H, aromatic protons), 4.50–4.25 (m, 4H, 2 CH$_2$), 3.80 (m, 2H, 2 CH), 3.40 (m, 4H, 2 CH$_2$), 2.30 (s, 6H, 2 CH$_3$) and 1.38 (d, 6H, 2 CH$_3$). MS (CI) m/e 625 (M+1). Anal. Calcd for C$_{32}$H$_{28}$N$_6$O$_8$.2CH$_3$SO$_3$H (MW 816.81) C, 50.00; H, 4.44; N, 10.09; S. 7.85. Found: C, 49.62; H, 4.42; N, 10.07; S, 7.80.

EXAMPLE 31

(R,R)-2,2'-[1,2-ethanediylbis[imino[2-methyl-2,1-ethanediyl]-bis[6-nitro-1H-benz[de]isoquinoline-1,3(2H)-dione] methanesulfonate (1:2) (XXVIIIb)

Yellow solid (17.0% yield); mp 230°–233° C. (dec). $^1$H-NMR (DMSO-d$_6$) δ9.03 (broad, 2H, NH$_2$+), 8.93 (broad, 2H, NH$_2$+), 8.76 (d, 2H, J=8.8 Hz, aromatic protons), 8.68–8.57 (m, 6H, aromatic protons), 8.13 (t, 2H, J=7.7 Hz, aromatic protons), 4.37–4.26 (m, 4H, 2 CH$_2$), 3.77 (m, 2H, 2 CH), 3.36 (s, 4H, 2 CH$_2$), 2.25 (s, 5.4H, 1.8 CH$_3$SO$_3$H) and 1.35 (d, 6H, 2 CH$_3$). MS (CI) m/e 625 (M+1). Anal. Calcd for C$_{32}$H$_{28}$N$_6$O$_8$.1.8CH$_3$SO$_3$H (MW 797.59) C, 50.90; H, 4.45; N, 10.54; S. 7.24. Found: C, 50.65, 50.56; H, 4.36, 4.36; N, 10.22, 10.18; S, 6.96, 6.96.

EXAMPLE 32

(R,R)-2,2'-[1,2-ethanediylbis[imino[2-methyl-2,1-ethanediyl)]-bis[5,8-dinitro-1H-benz[de]isoquinoline-1,3(2H)-dione] methanesulfonate (1:2) (XXIXb)

Light brown solid (21.1% yield); mp 227°–230° C. (dec). $^1$H-NMR (DMSO-d$_6$) δ9.84 (d, 4H, J=1.5 Hz, 4 aromatic protons), 9.13 (d, 4H, J=1.4 Hz, aromatic protons), 9.02 (broad, 2H, NH2+), 8.86 (broad, 2H, NH2+), 4.50–4.25 (m, 4H, 2 CH$_2$), 3.81 (m, 2H, 2 CH), 3.34 (broad, 4H, 2 CH$_2$), 2.24 (s, 6H, 2 CH$_3$) and 1.39 (d, 6H, J=4.7 Hz, 2 CH$_3$). Anal. Calcd for C$_{32}$H$_{28}$N$_6$O$_{12}$.2 CH$_3$SO$_3$H (MW 906.80) C, 45.03; H, 3.75; N, 12.36; S, 7.06. Found: C, 44.75; H, 3.69; N, 12.21; S, 6.87.

EXAMPLE 42

(Racemic)-2,2'-[1,2-ethanediylbis[imino]2-methyl-2,1-ethanediyl]-bis[5-nitro-1H-benz[de]isoquinoline-1,3(2H)-dione] methanesulfonate (1:2) (XXXIV)

The compound was prepared by mixing equal amounts of the corresponding (S,S) and (R,R) enantiomers (i.e., XIXa and XIXb, respectively). Light brown solid (90% yield); mp 254°–255° C. (dec). NMR spectrum is identical with those of XIXa and XIXb. Anal. Calcd for C$_{32}$H$_{28}$N$_6$O$_8$.2CH$_3$SO$_3$H (MW 816.81) C, 50.00; H, 4.44; N, 10.29; S, 7.85. Found: C, 49.69; H, 4.21; N, 10.19; S, 7.66.

EXAMPLE 43

(S,S,S)-5-nitro-2-[2-[[2-[[2-(5-nitro-1,3-dioxo-1H-benz[de]isoquinoline-2(3H)-yl)-1-methylethyl]amino]-1-methylethyl]anmino]-1-methylethyl]-1H-benz[de]isoquinoline-1,3(2H)-dione] methanesulfonate (1:2) (XXXX)

Part A: (XXXV) Methyl N-[N-[N-[(1,1-dimethylethoxy)carbonyl]-L-alanyl]-L-alanyl]-L-alanine.

To a THF solution (50 ml) of (t-BOC)-Ala-Ala-OH (5.0 g, 19.2 mmol) and N-methylmorpholine (3.88 g, 38.4 mmol), there was added isobutylchloroformate (2.62 g, 19.2 mmol) dropwise to maintain the temperature between 10° to 15° C. After addition was completed, the reaction mixture was stirred for another 15 minutes. To this, there was added 2.68 g (19.2 mmol) of (s)-alanine methyl ester hydrochloride. After stirring at ambient temperature overnight, the white N-methylmorpholine hydrochloride was removed by filtration; and the solvent in the filtrate evaporated. The remaining liquid was diluted with methylene chloride (350 ml), washed with 5% sodium bicarbonate (2×50 ml), water 1×150 ml), 0.1N HCl (1×150 ml), water 1×150 ml), brine (1×100 ml), dried over anhydrous magnesium sulfate, filtered and evaporated to give 4.32 g of a white solid, XXXV (65.1% yield): mp 168°–172° C. $^1$H-NMR (CDCl$_3$) δ6.70 (m, 2H, 2 NH), 4.98 (broad, 1H), 4.48 (m, 2H, 2 CH), 3.70 (s, 3H, CH$_3$), 1.38 (s, 18H, 6 CH$_3$) and 1.30 (m, 6H, 2 CH$_3$). MS (CI) m/e 346 (M+1). IR (KBr) 3391, 3319, 3275 (NH), 1742, 1710, 1674, 1638 (C=O) cm$^{-1}$. [α]$^{25}$ D−50.33° (C=0.600, CH$_2$Cl$_2$).

Part B: (XXXVI) N-[(1,1-dimethylethoxy)carbonyl]-L-alanyl-L-alanyl-L-alaninamide.

To 80 ml of methanol saturated with ammonia, there was added 2.75 g (7.96 mmol) of XXXV. The reaction mixture was cooled with an ice bath, and then further reacted with ammonia for 10 minutes. The reaction was stirred at ambient temperature overnight. The solvent in the solution was evaporated to give a yellow solid, XXXVI (2.45 g, 93% yield); mp 202°–208° C. $^1$H-NMR (DMSO-d$_6$) δ7.83–7.95 (m, 2H, 2 NH), 7.25 (broad, 1H, NH), 7.01 (broad, 2H, NH$_2$), 4.2 (m, 2H, 2 CH), 3.83 (m, 1H, CH) 1.38 (s, 9H, 3 CH$_3$) and 1.20 (m, 9H, 3 CH$_3$). MS (DCl) m/e 331 (M+1). [α]$^{25}$$_D$−6.00° (c=0.0600, DMSO).

Part C: (XXXVII) L-alanyl-L-alanyl-L-alaninamide hydrochloride.

A mixture of XXXVI (1.95 g, 5.9 mmol) and 4.4M HCl (2.68 ml) in dioxane was added to 40 ml of dioxane at 0° C. for 2 hr, and then warmed to room temperature overnight. The solvent in the mixture was evaporated to dryness to give 1.77 g of XXXVII as an off-white solid; mp 237°–240° C. (dec). $^1$H-NMR (D$_2$O) δ4.2–4.05 (m, 2H 2 CH), 2.95–3.85 (m, 1H, CH) and 1.25 (m, 9H, 3 CH$_3$). MS (CI) m/e 231 (M+1). IR (KBr) 3438, 3294 (NH$_2$), 1676, 1639 (C=O) cm$^{-1}$. [α]$^{25}$$_D$−19.96° (c=0.606, CH$_3$OH).

Part D: (XXXVIII) (S,S,S)-N$^1$-(2-amino-1-methylethyl)-N$^2$-(2-aminopropyl)-1,2-propanediamine tetrahydrochloride.

To a mixture of XXXVII (1.70 g, 6.37 mmol) in 150 ml of THF, there was added 58 ml of 1M BH$_3$•THF complex. The mixture was refluxed overnight to become a clear solution. The solution was cooled in an ice bath and quenched dropwise with 50 ml of methanol. The solution was refluxed overnight. The solvents in the reaction solution were removed by rotary evaporation. To the remaining liquid was added methanol (50 ml) and it was evaporated again to remove trimethylborate. The liquid was diluted with methanol (25 ml) followed by the addition of 4.0 ml of conc HCl. After stirring for 2 hr, this was triturated with ethyl ether, filtered to give 1.10 g (51.7% yield) of XXXVIII as a white solid; mp 277°–278° C. (dec). MS (DCl) m/e 189 (M+1). IR (KBr) 3436 (NH, NH$_2$) cm$^{-1}$.

Part E: (XXXIX) (S,S,S)-N$^1$-(2-amino-1-methylethyl)-N$^2$-(2-aminopropyl)-1,2-propanediamine.

To a freshly prepared sodium ethoxide solution (0.32 g of sodium of 20 ml of ethanol), there was added 1.05 g (3.1 mmol) of XXXVIII. The mixture was stirred at room temperature overnight. The sodium chloride was removed by filtration; and the solvent in the filtrate evaporated. The remaining liquid was purified by Kugelrohr distillation (0.4 mm, 94°-104° C.) to give 0.41 g of XXXIX as a light yellow liquid (70.2% yield) $^1$H NMR (CDCl$_3$) δ2.90 (m, 1H, CH), 2.80 (m, 2H, 2 CH), 2.53-2.30 (m, 6H, 3 CH$_2$), 1.58 (broad, 6H, 2 NH$_2$ and 2 NH) and 0.98 (m, 9H, 3 CH$_3$).

Part F: (XXXX) (S,S,S)-5-nitro-2-[2-[[2-[[2-(5-nitro-1,3-dioxo-1H-benz[de]isoquinoline-2(3H)-yl)-1-methylethyl]amino]-1-methylethyl]amino]1-methylethyl]-1H-benz[de]isoquinoline-1,3(2H)-dione] methanesulfonate (1:2).

A mixture of 3-nitro-1,8-naphthalic anhydride (1.06 g, 4.4 mmol) and XXXIX (0.41 g, 2.2 mmol) in 25 ml of ethanol was stirred at room temperature overnight and then heated to reflux for 1 ¼ hours. The solvent in the mixture was evaporated, and the remaining dark residue was purified by column chromatography to give 0.83 g of the free base as a light brown solid (59.1% yield), which was then converted to its methanesulfonate, XXXX (0.65 g; 35.6% yield); mp 189°-192° C. (shrink). $^1$H NMR (CDCl$_3$) δ9.28 (d, 1H, J=1.9 Hz, aromatic proton), 9.25 (d, 1H, J=2.2 Hz, aromatic proton), 9.15 (d, 1H, J=2.2 Hz, aromatic proton), 9.12 (d, 1H, J=2.2 Hz, aromatic proton, 8.81 (d, 1H, J=7.3 Hz, aromatic proton, 8.76 (d, 1H, J=7.3 Hz, aromatic proton), 8.46 (d, 1H, J=8.1 Hz, aromatic proton), 8.42 (d, 1H, J=8.4 Hz, aromatic proton), 7.98 (t, 1H, J=7.7 Hz, aromatic proton), 7.94 (t, 1H, J=7.92 Hz, aromatic proton), 5.76 (m, 1H, CH), 4.59 (m, 1H), 4.36 (m, 2H), 404 (m, 1H), 3.91 (m, 1H), 3.96 (m, 1H), 3.39 (m, 2H), 1.99 (s, 6H, 2 CH$_3$), 1.64 (d, 3H, J=7.0 Hz, CH$_3$), 1.54 (d, 3H, J=6.6 Hz, CH$_3$) and 1.48 (d, 3H, J=6.6 Hz, CH$_3$). MS (DCl) m/e 639 (M+1). Anal. Calcd for C$_{33}$H$_{30}$N$_6$O$_8$•2CH$_3$SO$_3$H (MW 830.44) c, 50.60; H, 4.61; N, 10.12; S, 7.72. Found: C, 50.70; H, 4.61; N, 9.98; S, 7.69.

TABLE 1

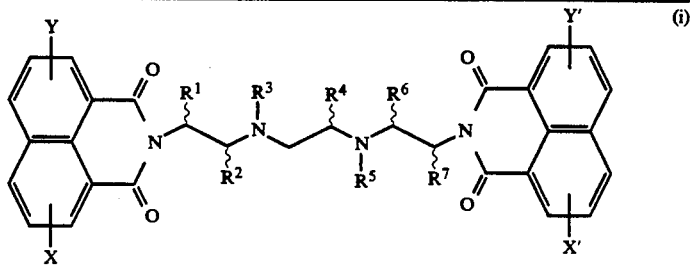

R$^2$, R$^3$, R$^4$, R$^5$, and R$^6$ = H

| Ex. | X, X' | Y, Y' | R$^1$, R$^7$ (stereochemistry) |
|---|---|---|---|
| 1 | 3-NO$_2$ | H | CH$_3$ (S) |
| 2 | 3-NO$_2$ | H | CH$_3$ (racemic + meso) |
| 3 | 3-NO$_2$ | H | CH$_3$ (R) |
| 5 | 3-NO$_2$ | 6-NO$_2$ | CH$_3$ (S) |
| 6 | 4-NO$_2$ | H | CH$_3$ (S) |
| 7 | 3-NO$_2$ | 6-NO$_2$ | CH$_3$ (R) |
| 8 | 4-NO$_2$ | H | CH$_3$ (R) |
| 26 | 3-NO$_2$ | H | CH$_3$ (meso) |

In Table 1 the position of X and Y is indicated using the numbering for the position in the corresponding naphthalic anhydride, and not the numbering for the 1H-benz[de]isoquinoline-1,3(2H)-dione.

TABLE 2

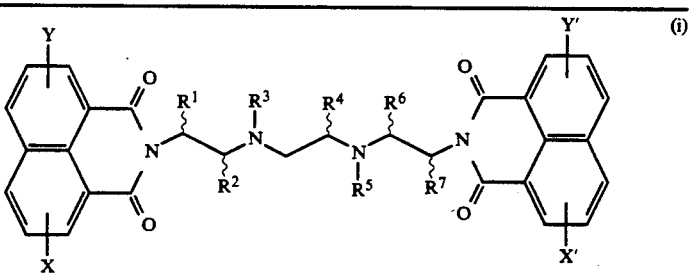

R$^1$, R$^3$, and R$^5$ = H

| Ex. | X, X' | Y, Y' | R$^2$, R$^6$ (stereochemistry) | R$^4$ | R$^7$ |
|---|---|---|---|---|---|
| 27 | 3-NO$_2$ | H | CH$_3$ (S) | H | H |
| 28 | H | H | CH$_3$ (S) | H | H |
| 29 | 3-NO$_2$ | H | CH$_3$ (R) | H | H |
| 30 | 3-NO$_2$ | H | CH$_3$ (racemic + meso) | H | H |
| 31 | 4-NO$_2$ | H | CH$_3$ (R) | H | H |
| 32 | 3-NO$_2$ | 6-NO$_2$ | CH$_3$ (R) | H | H |
| 42 | 3-NO$_2$ | H | CH$_3$ (racemic) | H | H |
| 43 | 3-NO$_2$ | H | R$^2$ = CH$_3$ (S); R$^6$ = H | CH$_3$ (S) | CH$_3$ (S) |

In Table 2 the position of X and Y is indicated using the numbering for the position in the corresponding naphthalic anhydride, and not the numbering for the 1H-benz[de]isoquinoline-1,3(2H)-dione.

UTILITY

In vitro Growth Inhibitory Activity

L1210 cells were maintained in RPMI-1640 a medium supplemented with 10% heat inactivated fetal bovine serum and 50 mL mercaptoethanol/liter medium (RPMI-L). B16 cells were maintained in RPMI-1640 medium supplemented with 15% heat inactivated fetal bovine serum and antiobiotics (RPMI-C).

Exponentially growing murine leukemia L1210 cells ($1 \times 10^3$ cells) in 0.1 mL medium were seeded on day 0 in a 96-well microtiter plate. On day 1, 0.1 μL aliquot of medium containing graded concentrations of test analogs was added to the initial volume. After incubation at 37° C. in a humidified incubator for 3 days, the plates were centrifuged briefly and 100 mL of the growth medium was removed. Cell cultures were incubated with 50 μL of 3-(4,5-dimethylthiazol-2-yl)-2,5-diphenyltetrazolium bromide (MTT; 1 mg/ml in Dulbecco's phosphate buffer saline) for 4 hours at 37° C. The resulting purple formazan precipitate was solubilized with 200 μL of 0.04N HCl in isopropyl alcohol. Absorbance was read in a Titertek Multiskan MCC scaning well spectrophotometer (Flow Laboratories) at a test wavelength of 570 nm and a reference wavelength of 630 nm.

The $ID_{50}$ values were determined by a computer program that fit all of the data (8 determinations per concentration and 12 concentrations per test analog) to the following equation:

$$Y = ((Am - Ao)/(1 + (X/ID_{50})n)) + Ao$$

where: Am=absorbance of the control cells; Ao=absorbance of the cells in the presence of highest drug concentration; Y=observed absorbance; X=drug concentration; $ID_{50}$=dose of drug that inhibits the growth of cells to one half that of the control cells.

Results of the in vitro L1210 growth inhibition testing are shown in Table 3.

TABLE 3

| Ex. No. | $ID_{50}$ (μg/ml) |
|---|---|
| 1 | 0.047 |
| 2 | 0.062 |
| 3 | 0.051 |
| 26 | 0.074 |
| 27 | 0.0025 |
| 28 | 0.21 |
| 29 | <0.01 |
| 30 | <0.01 |
| 31 | 0.19 |
| 32 | 0.057 |
| 42 | <0.001 |
| 43 | 0.04 |

In Vivo Tumor Models

Representative compounds of the present invention have been extensively tested in a variety of preclinical tests of anti-cancer activity which are indicative of clinical utility. For example, the presently claimed compounds show striking in vivo efficacy against three types of human tumors xenografted in nude mice, namely DLD-2 human colon carcimoma, MX-1 human mammary carcinoma, and LX-1 human lung carcinoma.

In addition, a representative compound of the present invention is active against several murine tumors, including murine M16c mammary adenocarcinoma and murine C51 colon adenocarcinoma. In addition, a representative compound of the invention is active against murine mammary tumors in transgenic mice containing the v-Ha-ras oncogene.

The methods used in the testing of compounds in the in vivo human tumor xenograft models are described below.

In Vivo Human Tumor Xenograft Models

The DLD-2 human colon tumor, MX-1 human mammary carcinoma, and LX-1 human lung tumor were originally obtained from a surgically removed primary colon carcinoma, breast tumor, and non-small lung carcinoma, respectively. The human tumor lines were maintained by serial passage in athymic nude mice. The MX-1 human mammary carcinoma and LX-1 human lung tumor are established tumors used by the NCI. The DLD-2, MX-1, and LX-1 tumor models have been well characterized.

The mice used in these experiments were outbred Swiss mice or BALB/c mice bearing the nude (nu/nu) gene. On day 0 male and female mice weighing 22-30 g are inoculated with 0.2 mL of a 25% tumor mince. This mince is prepared by mincing fresh tumor tissue, grown subcutaneously in passage mice, in sterile physiological saline. Palpable tumors weighing approximately 50 mg appear in the mice within 7-10 days after inoculation. The mice are pair matched by tumor weight and sex into groups of ten each and the test compounds and vehicle control are administered intravenously (i.v.) once daily for nine consecutive days. A >20% decrease in body weight on day 5 following compound administration is considered an indication of toxicity. Tumor measurements and body weights are recorded once a week. Fifteen to 18 days after the initial injection the mice are weighed, sacrificed and the tumors excised and weighed.

The efficacy of the test compounds is determined by the extent of tumor growth inhibition in treated versus vehicle-treated control mice. Initial tumor weights (mg) are calculated from the tumor dimensions (mm) measured from caliper measurements, using the formula for a prolate ellipsoid (mg of tumor weight=(length-$\times$width$^2$)/2). Net tumor weights are calculated for each of the treated groups and the vehicle-treated control group by subtracting the initial tumor weight from the final tumor weight on day 15. Results are expressed as a percentage decrease relative to the mean tumor weight for the control vehicle-treated group.

$$\% \text{ Tumor Growth Inhibition} = \left[1 - \frac{\text{mean tumor weight of treated}}{\text{mean tumor weight of control}}\right] \times 100$$

Activity Criteria

The criteria of the National Cancer Institute (NCI) for activity in the in vivo cancer models were used. Tumor growth inhibition of 58-89% in the DLD-2 assay is considered moderate activity and inhibition of ≧90% is considered good to excellent activity. Actual tumor regressions (IR=incomplete regression; FR=full regression) indicate excellent to outstanding activity. Compounds demonstrating <58% growth inhibition are considered inactive.

The compounds of Examples 1, 2, 3, 26, 27, and 30 exhibited excellent to outstanding activity against DLD-2 human colon tumors. Example 29 exhibited good to excellent activity against DLD-2 human colon tumors.

In addition, the compounds of Examples 2, 3, 27, 29, and 30 exhibited excellent to outstanding activity in the MX-1 human breast tumor model. Example 1 exhibited good to excellent activity against MX-1 human breast tumor.

Examples 2, 3, 27, and 29 exhibited good to excellent activity against LX-1 human lung tumors.

Activity Against Mammary Carcinomas in Transgenic Mice Containing the ras Oncogene Transgenic mice carrying the v-Ha-ras oncogene linked to the MMTV promoter were constructed originally in the laboratory of Professor Phil Leder at Harvard University (Sinn et al. (1987) Cell 49: 465–475). The female transgenic animals develop mammary tumors, and thus can be used to evaluate agents for activity against these breast tumors. The growth characteristics of these tumors has been characterized extensively (Diamond and Dexter (1991) Proc. Amer. Assoc. Cancer Res. 32: 299) and mimic the clinical situation.

Female ras-containing transgenic mice with breast tumors were treated i.v. with saline controls or with the test compound administered daily for 9 days and the group mean tumor growth rate for each test compound was monitored.

The demonstrated effectiveness of the compounds of the present invention in the human colon, breast, and lung tumor xenograft models indicate that the compounds of the present invention may be useful for the treatment of a broad spectrum of solid tumors in man, and, in particular, tumors of the colon, breast, and lung. This conclusion is further supported by published analyses correlating pre-clinical test results with clinical efficacy of anti-cancer agents. For example, see: Goldin and Venditti (1980) Recent Results Cancer Research 76: 176-191; Goldin et al. (1981) Eur. J. Cancer 17: 129–142; Mattern et al. (1988) Cancer and Metastasis Review 7: 263-284; Jackson et al. (1990) Cancer Investigations 8: 39–47. Based on these published analyses, the broad spectrum and exceptional high level of antitumor activity exhibited by the presently claimed compounds provide strong evidence that the compounds claimed in present invention may have important therapeutic utility in the treatment of cancer in man.

Dosage and Formulation

The antitumor compounds (active ingredients) of this invention can be administered to inhibit tumors by any means that produces contact of the active ingredient with the agent's site of action in the body of a mammal. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a tumor-inhibiting amount of active ingredient and will, of course, vary depending upon known factors such as the pharmacodynamic characteristics of the particular active ingredient, and its mode and route of administration; age, health, and weight of the recipient; nature and extent of symptoms; kind of concurrent treatment, frequency of treatment, and the effect desired. Usually a daily dosage of active ingredient can be about 5 to 400 milligrams per kilogram of body weight. Ordinarily, 10 to 200, and preferably 10 to 50, milligrams per kilogram per day given in divided doses 2 to 4 times a day or in sustained release form is effective to obtain desired results.

Dosage forms (compositions) suitable for internal administration contain from about 1.0 milligram to about 500 milligrams of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Useful pharmaceutical dosage forms for administration of the compounds of this invention can be illustrated as follows.

Capsules: Capsules are prepared by filling standard two-piece hard gelatin capsules each with 100 milligrams of powdered active ingredient, 175 milligrams of lactose, 24 milligrams of talc, and 6 milligrams magnesium stearate.

Soft Gelatin Capsules: A mixture of active ingredient in soybean oil is prepared and injected by means of a positive displacement pump into gelatin to form soft gelatin capsules containing 100 milligrams of the active ingredient. The capsules are washed and dried.

Tablets: Tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or delay absorption.

Injectable: A parenteral composition suitable for administration by injection is prepared by stirring 1.5% by weight of active ingredient in 10% by volume propylene glycol and water. The solution is made isotonic with sodium chloride and sterilized.

Suspension: An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

In the present disclosure it should be understood that the specified materials and conditions are important in practicing the invention but that unspecified materials and conditions are not excluded so long as they do not prevent the benefits of the invention from being realized.

What is claimed is:

1. A method for preparing a compound of the formula:

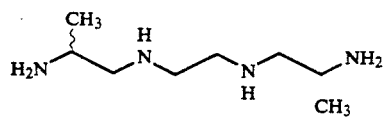

said method comprising:
(a) reacting t-BOC-alanine with 1,1' carbonyldiimidazole followed by reaction with ethylenediamine to yield a compound of the formula:

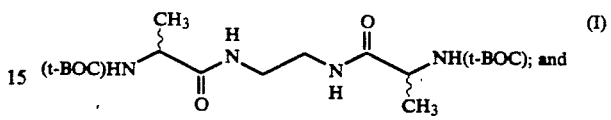

(b) removing the t-BOC group of (I) with mineral acid followed by reduction of the dihydrochloride salt with diborane in refluxing tetrahydrofuran followed by neutralization of the acid salt with sodium ethoxide to yield a compound of the formula (IV).

* * * * *